United States Patent [19]

Imhof et al.

[11] 4,272,627
[45] Jun. 9, 1981

[54] PHENYL-QUINOLIZINONES

[75] Inventors: René Imhof, Wittnau; Emilio Kyburz, Reinach, both of Switzerland

[73] Assignee: Hoffmann-La Roche Inc., Nutley, N.J.

[21] Appl. No.: 148,646

[22] Filed: May 12, 1980

Related U.S. Application Data

[62] Division of Ser. No. 85,096, Oct. 15, 1979.

[30] Foreign Application Priority Data

Oct. 13, 1978 [CH] Switzerland ............. 10654/78
Aug. 3, 1979 [CH] Switzerland ............. 7156/79

[51] Int. Cl.³ .................................. C07D 455/02
[52] U.S. Cl. .............................. 546/138; 548/336
[58] Field of Search ............................... 546/138

[56] References Cited

U.S. PATENT DOCUMENTS 3,429,884  2/1969  Matsuo et al. ............... 546/138
3,922,346  11/1975  Bruderlein et al. ........... 424/258

OTHER PUBLICATIONS

Chemical Abstracts, 75:77106v (1971) [Wrobel, J., et al., Rocz. Chem. 1971, 45(4), 705].

Chemical Abstracts, 83:131795z (1975) [Hanaoka, M., et al., Chem. Pharm. Bull. 1975, 23(7), 1573-1578].
Bruderlein, F., et al., J. Med. Chem., 18(2), 185-188 (1975).
Chemical Abstracts, 62:9103e (1965) [Bohlmann, F., et al., Tett. Lett. 1965(3), 167-170].
Chemical Abstracts, 64:15936g (1966) [Wrobel, J., et al., Roczniki Chem., 39(9), 1239-1244 (1965)].

Primary Examiner—Richard A. Schwartz
Attorney, Agent, or Firm—Jon S. Saxe; Bernard S. Leon; William G. Isgro

[57] ABSTRACT

Phenyl-quinolizidines of the formula

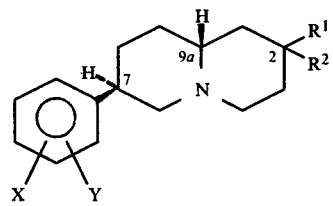

wherein $X, Y, R^1$ and $R^2$ are as hereinafter set forth, are described. The compounds of formula I are useful as antipsychotics, antiemetics and analgesics.

4 Claims, No Drawings

PHENYL-QUINOLIZINONES

This is a division of application Ser. No. 85,096, filed Oct. 15, 1979.

BRIEF SUMMARY OF THE INVENTION

The invention relates to phenyl-quinolizidines characterized by the formula

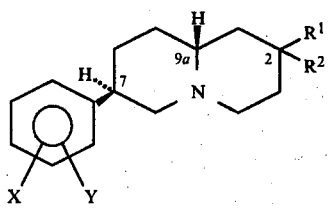

wherein X,Y,$R^1$ and $R^2$ are as described below:

X is hydrogen, fluorine, chlorine, lower alkoxy, lower alkyl or trifluoromethyl; Y is hydrogen, fluorine, chlorine, lower alkoxy or lower alkyl, preferably hydrogen; $R^1$ is hydroxy, lower alkoxy, acyloxy or, when $R^2$ is the group A defined hereinafter, hydrogen; and $R^2$ is lower alkyl, phenyl optionally substituted by halogen, lower alkoxy or trifluoromethyl, or when $R^1$ is hydrogen, a group A of the formula

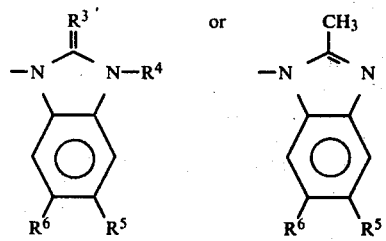

wherein $R^3$,$R^4$,$R^5$ and $R^6$ are as described below:

$R^3$ is oxygen or sulfur; $R^4$ is hydrogen or lower alkyl; $R^5$ and $R^6$ independently are hydrogen, methyl, fluorine, chlorine, methoxy or trifluoromethyl, or taken together are —$(CH_4)_4$—, as the racemates or the enantiomers, as well as the free bases and the acid addition salts thereof.

DETAILED DESCRIPTION OF THE INVENTION

The phenyl-quinolizidines of the invention are characterized by the formula

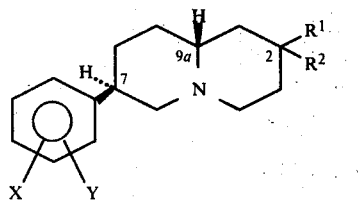

wherein X,Y,$R^1$ and $R^2$ are as described below:

X is hydrogen, fluorine, chlorine, lower alkoxy, lower alkyl or trifluoromethyl; Y is hydrogen, fluorine, chlorine, lower alkoxy or lower alkyl, preferably hydrogen; $R^1$ is hydroxy, lower alkoxy, acyloxy or, when $R^2$ is the group A defined hereinafter, hydrogen; and $R^2$ is lower alkyl, phenyl optionally substituted by halogen, lower alkoxy or trifluoromethyl, or, when $R^1$ is hydrogen, a group A of the formula

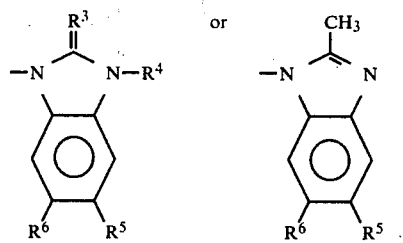

wherein $R^3$,$R^4$,$R^5$ and $R^6$ are as described below:

$R^3$ is oxygen or sulfur; $R^4$ is hydrogen or lower alkyl; $R^5$ and $R^6$ independently, are hydrogen, methyl, fluorine, chlorine, methoxy or trifluoromethyl, or taken together, are —$(CH_2)_4$—, in the form of their racemates or their enantiomers, as well as in the form of the free bases or in the form of the acid addition salts.

As shown in formula I and in various of the other formulas, the hydrogen atoms in the 7- and 9a-positions are in trans relationship to one another, whereby in the formulas the hydrogen atom in the 9a-position is arbitrarily shown in the β-position and the hydrogen atom in the 7-position is correspondingly shown in the α-position. The relative configuration shown for the phenyl-quinolizidines of formula I of the invention as well as the corresponding intermediates and starting materials is not intended to exclude, and in fact embraces, the corresponding enantiomeric forms, namely, compounds having hydrogen atoms in the 9aα- and 7β-positions, as well as the racemates of these two enantiomeric forms. Similarly, with reference to the configuration in the 2-position of the phenyl-quinolizidines, it is not intended to exclude the racemates or enantiomers. Thus, for example, in formula III hereinafter, the hydrogen atoms in the 2- and 9a-positions are shown in the β-position and the hydrogen atom in the 7-position is shown in the α-position, then accordingly the relative configuration at these three asymmetric centers is specified (9aH to 7H: trans; 9aH to 2H: cis), but the absolute configuration is not specified and either enantiomer is intended.

The lower alkyl and lower alkoxy groups referred to herein are alkyl and alkoxy groups, respectively, which contain 1–6, preferably 1–4, carbon atoms, the groups containing 3 and more carbon atoms being straight-chain or branched-chain. An acyloxy group referred to as a possible $R^1$-substituent can be derived from an organic, saturated or unsaturated, optionally substituted carboxylic acid, preferably an optionally halogen-substituted lower alkanecarboxylic acid, such as acetic acid, trifluoroacetic acid or the like.

As acid addition salts of the phenyl-quinolizidines of the invention there come into consideration pharmacologically compatible salts with the organic and inorganic acids customarily used for salt formation. Examples of such acids are mineral acids, for example, sulfuric acid, nitric acid, phosphoric acid and hydrohalic acids, such as hydrochloric acid and hydrobromic acid, and organic acids, for example, tartaric acid, citric acid, aliphatic or aromatic sulfonic acids, maleic acid, mandelic acid, and the like. The salt formation can be carried out in a known manner.

It is noted that the compounds of formula I embrace the following sub-groups:

(a) alkyl- or aryl-carbinols of the formula

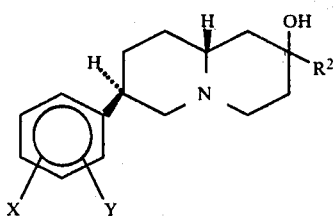

preferably those of the formula.

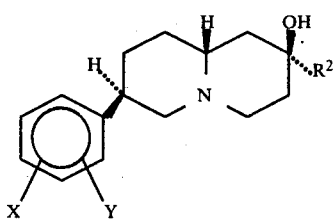

wherein X, Y and $R^2$ are as previously described, in racemic form and in the form of the enantiomers, as well as, if desired, in the form of acid addition salts, (b) the esters and ethers of the carbinols set forth under (a), that is, the compounds of the formula

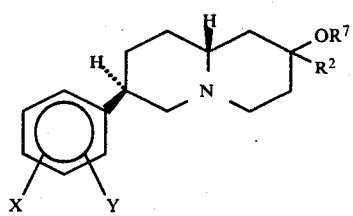

wherein X, Y and $R^2$ are as previously described, and $R^7$ is lower alkyl or acyl, in racemic form and in the form of the enantiomers, as well as, if desired, in the form of acid addition salts, (c) the benzimidazoline and benzimidazolinethione derivatives of the formula

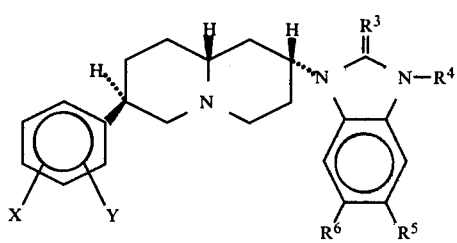

wherein X,Y,$R^3$,$R^4$,$R^5$ and $R^6$ are as previously described, in racemic form and in the form of the enantiomers, as well as, if desired, in the form of acid addition salts, and (d) the methylbenzimidazole derivatives of the formula

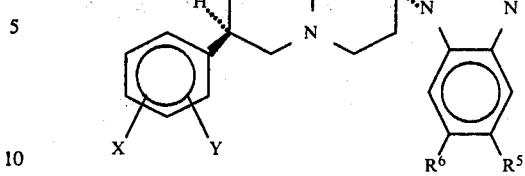

wherein X,Y,$R^5$ and $R^6$ are as previously described, in racemic form and in the form of the enantiomers, as well as, if desired, in the form of acid addition salts.

The compounds of formula II hereinbefore have predominantly neuroleptic activity. Preferred amongst these are the compounds of formula II-1 hereinbefore, in particular those in which $R^2$ is branched-chain lower alkyl, X is fluorine or chlorine and Y is hydrogen, fluorine or chlorine, X and Y are present in the ortho- and-/or para-position, predominantly because of their neuroleptic activity. Especially preferred compounds of formula II-1 are those wherein $R^2$ is tert.butyl, X is o-chloro and Y is p-chloro or $R^2$ is tert.butyl, X is p-trifluoromethyl and Y is hydrogen.

The compounds of formula IV hereinbefore are preferred predominantly because of their analgesic activity. Especially preferred compounds of formula IV are those in which (a) X and Y are hydrogen, $OR^7$ is acetoxy and has the same orientation as the 9a-hydrogen and $R^2$ is n-butyl, (b) X and Y are hydrogen, $OR^7$ is trifluoroacetoxy and has the same orientation as the 9a-hydrogen atom and $R^2$ is tert.butyl, or (c) X is o-chloro, $R^2$ is phenyl and has the same orientation as the 9a-hydrogen atom and $OR^7$ represents acetoxy.

The compounds of formulas III-1 and III-2 hereinbefore have predominantly neuroleptic activity. The benzimidazolinone and benzimidazolinethione derivatives of formula III-1 in which X is hydrogen, o-fluoro or o-chloro, Y is hydrogen, $R^3$ is oxygen or sulfur, $R^4$ is hydrogen, $R^5$ is fluorine, chlorine or trifluoromethyl and $R^6$ is hydrogen, chlorine or fluorine are preferred. The following compounds of formula III-1 are especially preferred:

(a) X=o—Cl; Y, $R^4$, $R^5$, $R^6$=H; $R^3$=O,
(b) X=o—Cl, Y, $R^4$=H; $R^3$=O; $R^5$, $R^6$=CH$_3$,
(c) X=o—Cl; Y, $R^4$=H; $R^3$=O; $R^5$, $R^6$=Cl,
(d) X=o—Cl; Y, $R^5$, $R^6$=H; $R^3$=O; $R^4$=CH$_3$,
(e) X=o—Cl; Y, $R^4$, $R^6$=H; $R^5$=CF$_3$; $R^3$=O,
(f) X=o—Cl; Y, $R^4$, $R^6$=H; $R^5$=Cl; $R^3$=O,
(g) X=o—Cl; Y, $R^4$, $R^6$=H; $R^5$=Cl; $R^3$=S,
(h) X=o—Cl; Y, $R^4$=H; $R^3$=S, $R^5$, $R^6$=Cl,
(i) X=o—Cl; Y, $R^4$=H; $R^3$=O; $R^5$ and $R^6$ together-=—(CH$_2$)$_4$—,
(j) X=o—F; Y, $R^4$=H; $R^3$=O, $R^5$, $R^6$=CH$_3$,
(k) X=o—F; Y, $R^4$=H; $R^3$=O; $R^5$, $R^6$=Cl,
(l) X=o—F; Y, $R^4$=H; $R^3$=S; $R^5$, $R^6$=Cl,
(m) X=o—F; Y, $R^4$=H; $R^3$=O; $R^5$ and $R^6$ together-=—(CH$_2$)$_4$—,
(n) X=o—F; Y, $R^4$, $R^6$=H; $R^5$=CF$_3$; $R^3$=O,
(o) X=o—F; Y, $R^4R^6$=H; $R^5$=CF$_3$; $R^3$=S,
(p) X=o—F; Y, $R^4$, $R^6$=H; $R^5$=Cl; $R^3$=O,
(q) X=o—F; Y, $R^4$, $R^6$=H; $R^5$=Cl; $R^3$=S.

In accordance with the process of the invention, the phenyl-quinolizidines aforesaid are prepared by (1) for the preparation of compounds of the formula

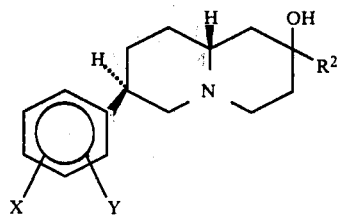
II wherein X, Y and $R^2$ are as previously described, either (a) reacting a ketone of the formula

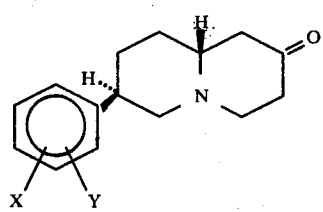
V wherein X and Y are as previously described, with a metal-organic compound yielding the group $R^2$ and, if desired, separating the mixture of diastereomers obtained, or (b) adding water at the $\Delta^1$- or $\Delta^2$-double bond present in a comopound of the formula

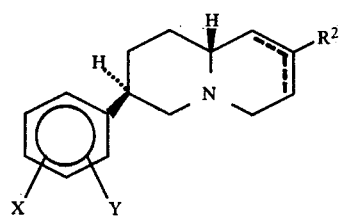
VI wherein X, Y and $R^2$ are as previously described, and the broken line denotes a double-bond in the 1,2- or 2,3-position, by reaction with a hydrating agent, or (2) for the preparation of compounds of the formula

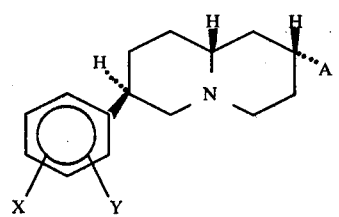
III wherein X, Y and A are as previously described, reacting a compound of the formula

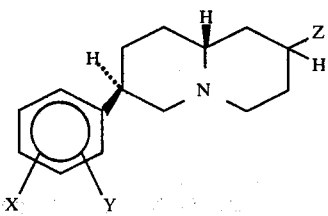
VII wherein X and Y are as previously described, and Z is a cleavable group, with a compound of the formula

H—A
VIII wherein A is as previously described, or (3) for the preparation of a compound of the formula

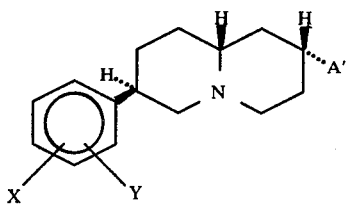
III-3 wherein X and Y are as previously described and A' has any of the values accorded to A hereinbefore except that $R^3$ is oxygen, catalytically hydrogenating a compound of the formula

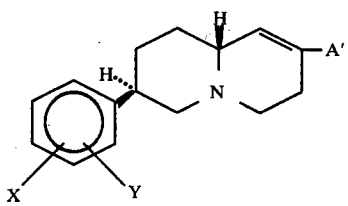
IX wherein X, Y and A' are as previously described, or (4) for the preparation of a compound of the formula

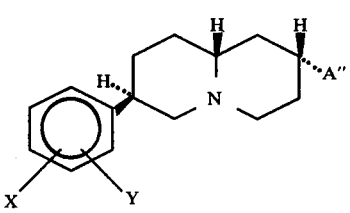
III-4 wherein X and Y are as previously described and A'' has any of the values according to A hereinbefore with the exception that $R^3$ is oxygen and $R^4$ is hydrogen, condensing a phenylenediamine of the formula

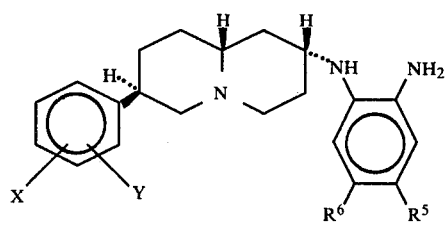
X wherein X, Y, $R^5$ and $R^6$ are as previously described, with a cyclizing agent of the formula

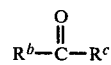
XI wherein $R^b$ and $R^c$ are halogen, amino or 1-imidazolyl, or with acetic acid or an orthoacetic acid ester, or (5) for the preparation of a compound of the formula

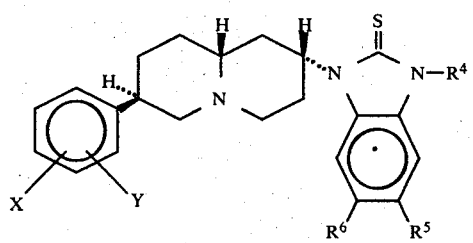

III-5 wherein X, Y, R⁴, R⁵ and R⁶ are as previously described, either (a) reacting a corresponding oxo compound of the formula

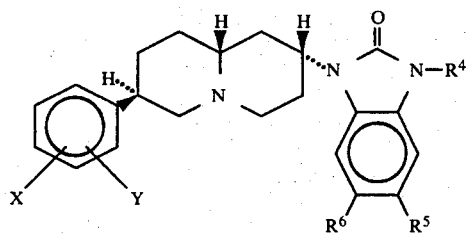

III-6 wherein X, Y, R⁴, R⁵ and R⁶ are as previously described, with phosphorus pentasulfide, or (b) reacting a phenylene-diamine of formula X hereinbefore with thiophosgene, thiocarbonyldiimidazole or carbon disulfide and, if desired, N-alkylating the reaction product, or (6) for the preparation of compounds of the formula

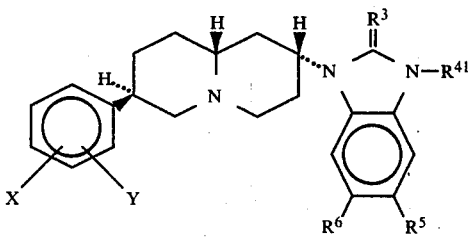

III-7 wherein X, Y, R³, R⁵ and R⁶ are as previously described and R⁴¹ is lower alkyl, N-alkylating a compound of the formula

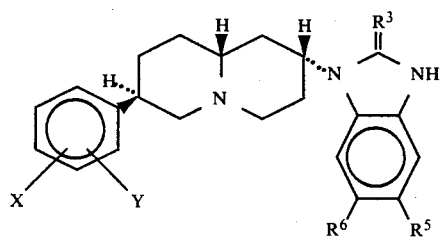

III-8 wherein X, Y, R³, R⁵ and R⁶ are as previously described, or (7) for the preparation of ethers and esters of the formula

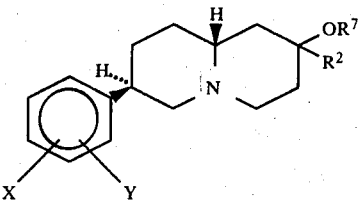

IV wherein X, Y, R² and R⁷ are as previously described, reacting an alcohol of formula II hereinbefore with an etherifying or esterifying agent yielding the group R⁷ and, if desired, cleaving a racemate obtained and, also if desired, converting a base obtained into an acid addition salt.

All of the reactions specified in the aforementioned process embodiments (1) to (7) can be carried out according to known methods.

For the conversion of a ketone of formula V into a tertiary carbinol of formula II in accordance with process embodiment (1)(a) there can be used the customary metal-organic compounds yielding the group R² such as the corresponding Grignard compounds of the formula R²-Mg-halogen, R²-lithium compounds or R²-lithium-copper compounds.

A third asymmetric center (in the 2-position) occurs when a carbinol is prepared from a ketone of formula V. The newly introduced group R² can in this case occupy the cis- and/or trans-position in relation to the 9a-hydrogen atom. Thus, for example, from a racemic ketone of formula V there are obtained as described in Example 3 hereinafter two diastereomeric carbinols of formula II, each as the racemate, while from a racemic ketone of formula V there is obtained, as described in Example 1 hereinafter, of the two theoretically possible diastereomeric racemates of formula II, practically only the one racemate, namely, that in which R² is in the trans-position to the 9a-hydrogen atom, which compound is characterized by formula II-1.

Diastereomeric mixtures obtained as well as racemates obtained can be separated or cleaved according to known methods.

Water at the Δ¹- or Δ²-double bond of a compound of formula VI can be added, in accordance with process embodiment (1)(b) using as the hydrating agent, for example, aqueous sulfuric acid.

For the preparation of benzimidazole derivatives of formula III, in accordance with process embodiment (2), a compound of formula VII which contains, for example, a chlorine or bromine atom or a mesyloxy or tosyloxy group as the cleavable group can be reacted with a compound of formula VIII, preferably in the form of an alkali metal salt.

For the preparation of the benzimidazole derivatives of formula III-3 according to process embodiment (3), the Δ¹-double bond present in a compound of formula IX can be catalytically hydrogenated. As the catalyst, there can be used a customary hydrogenation catalyst, such as platinum oxide, palladium/carbon, for example, 10%, or the like.

For the preparation of the benzimidazole derivatives of formula III-4 according to process embodiment (4), a phenylene-diamine of formula X can be reacted with a cyclizing agent of formula XI, for example, phosgene, carbonyldiimidazole, urea, or the like, to give a benzimidazolinone derivative of formula III-1 or with acetic acid or an orthoacetic acid ester, for example, the trimethyl or triethyl ester, to give a methylbenzimidazole derivative of formula III-2.

For the preparation of the thiones of formula III-3, in accordance with process embodiment (5)(a), the oxygen atom present in the imidazole ring of an oxo compound of formula III-6 can be replaced by a sulfur atom using phosphorus pentasulfide in accordance with known methods, or in accordance with process embodiment (5)(b), a phenylene-diamine of formula X can be reacted with thiophosgene, thiocarbonyldiimidazole or carbon disulfide in a known manner. The subsequent, optional N-alkylation at $R^4$ is effected in an analogous manner to that described hereinafter in connection with process embodiment (6).

Embodiments (4) and (5)(b) are especially well suited to the preparation of compounds of formula III-4 or III-5 in which $R^5$ is different from $R^6$.

For the preparation of compounds III-7 which are N-alkylated in the imidazole ring according to process embodiment (6), there can be used a customary N-alkylating agent, such as a lower alkyl halide, for example, methyl iodide.

For the preparation of the ethers and esters of formula IV according to process embodiment (7), a carbinol of formula II can be esterified in a known manner, for example, by reaction with an acid anhydride of the formula $(R^7CO)_2O$ in the presence of pyridine or with an isopropenyl ester of the formula $CH_2=C(CH_3)O-CO-R^7$ in the presence of p-toluenesulfonic acid, or etherified in a known manner by reaction with a lower alkyl halide, basic etherification, or an $R^7OH$/sulfuric acid mixture, acidic etherification.

The compounds referred to hereinafter as intermediates or starting materials, insofar as they are not known, can be prepared according to known methods. Thus, for example, the ketone starting materials of formula V used in process embodiment (1)(a) can be prepared in a known manner by decarboxylating β-keto-esters of formula XIV with the relative configuration with respect to the 1-,7- and 9a-positions indicated in the formula which follows:

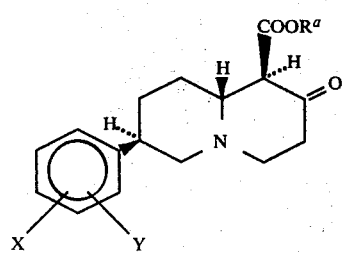
XIV wherein X and Y are as previously described and $R^a$ is lower alkyl, see, for instance, Example 1(b).

The β-keto-esters of formula XIV can, in turn, be prepared from the corresponding unsaturated β-keto-esters of the formula

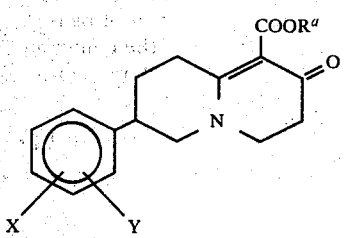
XIII wherein X, Y and $R^a$ are as previously described, in a known manner by hydrogenation [see, for instance, Example 1(c)].

The β-keto-esters of formula XIII can be prepared from corresponding 5-phenyl-2-piperidones which are optionally substituted in the phenyl ring according to known methods, see, for instance, Example 1(d).

The benzimidazolines of formula III-8 used as starting materials in process embodiment (6) can be prepared by hydrogenating the corresponding unsaturated compounds of formula XV, with the relative configuration in the 7- and 9a-positions indicated in the formula which follows:

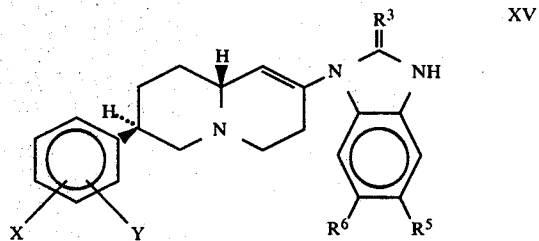
XV wherein X, Y, $R^3$, $R^5$ and $R^6$ are as previously described.

By N-alkylating compounds of formula XV in a manner analogous to that described in connection with process embodiment (6), there are obtained N-alkylated starting materials of formula IX.

The compounds of formula XV can, in turn, be prepared from the aforementioned β-keto-esters of formula XIV according to the process described in Example 7b or in analogy thereto.

The compounds of formulas VI and VII hereinbefore can be prepared according to the process described in Examples 13 and 14 or in analogy thereto.

The intermediates or starting materials of formulas V, VI, VII, IX, X, XIII, XIV and XV are new and therefore also form part of the invention.

The phenyl-quinolizidines of formula I provided by the invention possess valuable pharmacological properties. More specifically, the phenyl-quinolizidines of formula I demonstrate central-depressant, tranquilizing and antiemetic activity. Further, as hereinbefore set forth, various subgroups of compounds of formulas II and III have neuroleptic activity, and the compounds of formula IV have analgesic activity. Therefore, the compounds of formula I can be used as central-depressant, tranquilizing and antiemetic agents. The subgroups characterized by formulas II and III can also be used as neuroleptic agents, and the subgroup characterized by formula IV can also be used as analgesic agents. Accordingly, the neuroleptic compounds can be used as antipsychotics in the treatment of psychoses and neuroses, the analgesic compounds can be utilized in the control of pain, and the compounds having antiemetic activity can be utilized in the control of nausea.

The neuroleptic properties of the compounds of formula I of the invention were determined numerically using the tests described hereinafter:

"POLE CLIMBING" TEST (RAT)

In this test, there was used, for each dosage, a group of 10 rats which had been trained to escape an electric shock, unconditioned stimulus, produced via the lattice floor immediately after an acoustic signal, conditioned stimulus, by jumping up a vertical isolated pole in the experimental cage. The inhibition of the conditioned reaction in 50% of the rats during an observation time of 6 hours is defined by the parameter ED 50 BCR (Block of Conditioned Reflex) and the inhibition of the unconditioned reaction is defined by the parameter ED 10 BUR (Block of Unconditioned Reflex).

SPIROPERIDOL-BINDING TEST (IN VITRO)

In this in vitro test calf striatum was used as the receptor [Creese et al., Life Sci. 17, 993 (1975)] and incubated with [$^3$H] spiroperidol in analogy to the method described by Fields et al., Brain Research 136, 578 (1977). The IC 50, which is the concentration of the test substance at which a 50% detachment of the specific binding of [$^3$H] spiroperidol on the receptor takes place, was determined from four different concentrations in a triple procedure, using a computer program.

Representative experimental results are compiled in Table A hereinafter:

TABLE A

| Compound | Pole-Climbing BCR ED$_{50}$ i.p. (mg/kg) | Pole-Climbing BUR ED$_{10}$ i.p. (mg/kg) | Spiroperidol-binding IC$_{50}$ (nanomolar) |
|---|---|---|---|
| rac-(9aβH)-2α-tert.-Butyl-7β-(2,4-dichlorophenyl)octahydro-2H-quinolizin-2-ol HCl | 6.4 | 5.4 | 79 |
| (−)-(2S,7R,9aR)-2-tert.-Butyl-7-(2,4-dichlorophenyl)octahydro-2H-quinolizin-2-ol HCl | 4.7 | 3.8 | 41 |
| rac-1-[(9aβH)-7β-(o-Chlorophenyl)octahydro-2H-quinolizin-2α-yl]-5,6-dimethyl-2-benzimidazolinone HCl | 1.75 | 4.55 | 5 |
| rac-1-[(9aβH)-7β-(o-Chlorophenyl)octahydro-2H-quinolizin-2α-yl]-5-trifluoromethyl-2-benzimidazolinone HCl | 0.21 | 0.41 | 10 |
| rac-1-[(9aβH)-7β-(o-Fluorophenyl)octahydro-2H-quinolizin-2α-yl]-5-chloro-2-benzimidazolinone HCl | 0.064 | 0.175 | |

The analgesic properties of the compounds of formula I provided by the invention were determined numerically using the tests described hereinafter:

WRITHING TEST (MOUSE)

Eight male mice (20-22 g.) per dosage, were used for this test. Sixty minutes after oral administration of the test substance, the mice were injected intraperitoneally with 10 ml/kg of the test solution. Following a latent period of 5 minutes, the number of animals in which no more than one characteristic writhing symptom (convulsive stretching movement of the body) occurred over five minutes was registered. The ED 50 is the dosage at which 50% of the mice show no more than one writhing.

HOT-PLATE TEST (MOUSE)

Eight mice (20-22 g) were used per dosage. Sixty minutes after oral administration of the test substance, the mice were placed on a heated metal plate of 60°±0.5° C. Untreated mice begin to lick their paws within a maximum of 10 seconds. The ED 50 is defined as the dosage at which 50% of the mice begin to lick their paws only after a latent period of more than 10 seconds.

Representative experimental results are compiled in Table B hereinafter:

TABLE B

| Compound | Writhing 60' ED$_{50}$ p.o. mg/kg | Hot-plate 60' ED$_{50}$ p.o. mg/kg |
|---|---|---|
| (+)-2-Butyloctahydro-7-phenyl-2H-quinolizin-2-yl acetate HCl | 0.19 | 2.6 |
| rac-(9aβH)-2α-n-Butyl-7β-phenyl-octahydro-2H-quinozilin-2-yl acetate HCl | 0.75 | 25 |
| rac-(9aβH)-2α-tert.Butyl-7β-phenyl-octahydro-2H-quinolizin-2-yl trifluoro-acetate HCl | 8.7 | 86 |
| rac-(9aβH)-2α-Phenyl-7β-(m-methoxyphenyl)-octahydro-2H-quinolizin-2-yl propionate HCl | 2.8 | 12 |
| rac-(9aβH)-2β-Phenyl-7β-(o-chlorophenyl)-octahydro-2H-quinolizin-2-yl acetate HCl | 116 | 284 |

The phenyl-quinolizidines of formula I provided by the present invention can be used as medicaments, for example, in the form of pharmaceutical preparations. The pharmaceutical preparations can be administered orally, for example, in the form of tablets, coated tablets, dragees, hard and soft gelatin capsules, solutions, emulsions, suspensions or the like. The pharmaceutical preparations can, however, also be administered rectally, for example, in the form of suppositories; locally or percutaneously, for example, in the form of salves, creams, gels or solutions; or parenterally, for example, in the form of injectable solutions.

For the preparation of tablets, coated tablets, dragees and hard gelatin capsules, the phenyl-quinolizidines of formula I can be processed with pharmaceutical inert, inorganic or organic excipients. Exemplary of excipients which can be used for tablets, dragees and hard gelatin capsules are lactose, maize starch or derivatives thereof, talc, stearic acid or salts thereof, or the like. Suitable excipients for soft gelatin capsules are, for example, vegetable oils, waxes, fats, semi-solid, liquid polyols or the like. While no excipients are generally required, in the case of soft gelatin capsules, an excipient may be necessary due to the nature of the active ingredient. Suitable excipients for the preparation of solutions and syrups are, for example, water, polyols, saccharose, invert sugar, glucose and the like. Suitable excipients for injectable solutions are, for example, water, alcohols, polyols, glycerine, vegetable oils, or the like. Suitable excipients for suppositories, or for local or percutaneous administration forms are, for example, natural or hardened oils, waxes, fats, semi-liquid or liquid polyols or the like.

The pharmaceutical preparations can, moreover, also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances.

In the aforementioned pharmaceutical preparations, the dosages at which the compounds of formula I can be administered can lie in the approximate range of 0.5-100 mg. In the case of oral administration, a dosage of a compound of formula I of about 0.05 mg/kg to about 10 mg/kg per day comes into consideration and in the case of parenteral administration, a dosage of a compound of formula I of about 0.01 mg/kg to 1 mg/kg per day comes into consideration.

The following Examples further illustrate the invention. All temperatures are stated in degrees Centigrade, unless otherwise mentioned.

EXAMPLE 1

(a) 22.2 g. of rac-(9aβ H)-7 β-(o-chlorophenyl)octahydro-2H-quinolizin-2-one dissolved in 300 ml. of absolute tetrahydrofuran are added dropwise under argon with strong stirring to a solution, cooled to −75° C., of tert.butyllithium in pentane (100 ml; 1.2 molar). Subsequently, the mixture is left at −75° C. for a further 30 minutes and then worked up as follows: The mixture is hydrolyzed by adding 100 ml. of saturated ammonium chloride solution and is then partitioned between ethyl acetate and water. After repeated extraction with ethyl acetate, the entire organic phase is dried over magnesium sulfate and evaporated. From the residue the end product [rac-(9aβ H)-2α-tert.butyl-7 β-(o-chlorophenyl)octahydro-2H-quinolizin-2-ol] can be crystallized as the hydrochloride salt from 1400 ml. of ethyl acetate by conducting in gaseous hydrogen chloride; yield 20.4 g (71%); melting point 276°-278° C. An alternative purification procedure comprises chromatographing the residue on silica gel with ether/hexane (1:1).

When in place of rac-(9aβ H)-7β-(o-chlorophenyl)octahydro-2H-quinolizin-2-one there are used equimolar amounts of corresponding substituted ketones, the following tert.butylcarbinols can be obtained:

TABLE 1

| rac-(9aβH)-2α-Tert.butyl-7β-(R$_a$)octahydro-2H-quinolizin-2-ol: | | | |
|---|---|---|---|
| | | | M.p. °C. |
| R$_a$ = | phenyl | HCl salt | 230 (dec.) |
| | p-chlorophenyl | HCl salt | 286-288 |
| | 2,4-dichlorophenyl | HCl salt | 270-272 |
| | 2,6-dichlorophenyl | HCl salt | 262-263 |
| | p-trifluoromethylphenyl | HCl salt | 285-286 |

When in place of tert.butyllithium equimolar amounts of analogous alkyl- or aryllithium reagents are reacted with the corresponding ketones, the following carbinols can be obtained:

TABLE 2

| rac-(9aβH)-(R$_b$)-7β-(R$_a$)octahydro-2H-quinolizin-2-ol: | | | |
|---|---|---|---|
| | | | M.p. °C. |
| R$_b$ = 2α-sec.butyl | R$_a$ = 2,4-dichlorophenyl | HCl salt | 244-246 |
| 2α-n-butyl | R$_a$ = 2,4-dichlorophenyl | " | 227-230 |
| 2α-isopropyl | R$_a$ = 2,4-dichlorophenyl | " | 201-205 |

TABLE 2-continued

| rac-(9aβH)-(R$_b$)-7β-(R$_a$)octahydro-2H-quinolizin-2-ol: | | | |
|---|---|---|---|
| | | | M.p. °C. |
| 2(α + β)-methyl | R$_a$ = 2,4-dichlorophenyl | " | 149-151 |
| 2α-n-butyl | phenyl | base | 100-102 |
| 2α-phenyl | o-chlorophenyl | HCl salt | 266-267 |
| 2β-phenyl | " | " | 175° amorphous |
| 2α-phenyl | m-methoxyphenyl | base | 153-155 |
| 2β-phenyl | " | " | 122-124 |
| 2α-phenyl | phenyl | " | 156-158 |
| 2β-phenyl | " | " | 99-102 |
| 2α-m-methoxyphenyl | " | $^1$H-NMR | (CDCl$_3$): 3.77 (s) |
| 2β-m-methoxyphenyl | " | $^1$H-NMR | (CDCl$_3$): 3.82 (s) |
| 2α-p-chlorophenyl | " | HCl salt | 249-250 |
| 2α-m-trifluoromethylphenyl | p-chlorophenyl | base | 119-123 |
| 2β-m-trifluoromethylphenyl | " | " | 122-124 |

(b) The rac-(9aβH)-7β-(o-chlorophenyl)octahydro-2H-quinolizin-2-one used as the starting material can be prepared as follows:

76.2 g. of methyl rac-(1αH,9aβ H)-7β-(o-chlorophenyl)-octahydro-2-oxo-2H-quinolizine-1-carboxylate are dissolved in 1.2 liters of 6 N hydrochloric acid and boiled at reflux for 3 hours. The cooled solution is subsequently poured on to ice and made alkaline with concentrated sodium hydroxide. Extraction with three 500 ml. portions of methylene chloride and evaporation of the organic phase, dried over magnesium sulfate, gives 68 g. of crude product. 50.4 g. of rac-(9aβ H)-7β-(o-chlorophenyl)octahydro-2H-quinolizin-2-one can be crystallized from ether/hexane; melting point 80°-82° C. (81%).

When in place of methyl rac-(1αH,9aβ H)-7β-(o-chlorophenyl)octahydro-2-oxo-2H-quinolizine-1-carboxylate equimolar amounts of corresponding substituted β-keto-esters are decarboxylated, the following products are obtained:

TABLE 3

| rac-(9aβH)-7β-(R$_a$)octahydro-2H-quinolizin-2-one: | | |
|---|---|---|
| | | M.p. °C. |
| R$_a$ = phenyl | | 71-72 |
| p-chlorophenyl | | 80-82 |
| p-trifluoromethylphenyl | | 103-104 |
| o-methylphenyl | IR (film) | 1726 cm$^{-1}$ |
| m-methoxyphenyl | IR (film) | 1726 cm$^{-1}$ |
| 2,4-dichlorophenyl | | 116-117 |
| 2,6-dichlorophenyl | | 116-118 |
| o-fluorophenyl | | 74-76 |

(c) The octahydro-carboxylate used as the starting material in paragraph 1(b) can, in turn, be prepared from the corresponding hexahydro-carboxylate as follows:

180 g of methyl rac-7-(o-chlorophenyl)-3,4,6,7,8,9-hexahydro-2-oxo-2H-quinolizine-1-carboxylate are suspended in 3.6 liters of monoglyme (dimethoxyethane), cooled to −30° C. and 1.33 liters of DIBAH (diisobutylaluminum hydride, 20% solution in toluene) are added while stirring. Subsequently, the mixture is stirred for 1 hour at −20° C. to −30° C. and then hydrolyzed at this temperature with 1.72 liters of 2 N sodium hydroxide. For the working-up, the mixture is partitioned between 25 liters of water and 20 liters of chloroform, the organic phase is washed with two 5 liter portions of water, dried over magnesium sulfate and evaporated, there being obtained 185.2 g of crude product. 109 g of product can be crystallized from ether/hexane. By chromatography of the mother liquor on 1 kg of silica gel with ethyl acetate there are obtained 37 g of product. The total yield of methyl rac-(1αH,-9aβH)-7β-(o-chlorophenyl)-octahydro-2-oxo-2H-quinolizine-1-carboxylate is 136 g (81%); melting point 122°–124° C.

When in place of methyl rac-7-(o-chlorophenyl)-3,4,6,7,8,9-hexahydro-2-oxo-2H-quinolizine-1-carboxylate equimolar amounts of correspondingly substituted educts are reduced with DIBAH, the following compounds are obtained:

TABLE 4

Methyl rac-(1αH,aβH)-7β-(R$_a$)octahydro-2-oxo-2H-quinolizine-1-carboxylate:

|  |  | M.p. °C. |
|---|---|---|
| R$_a$ = phenyl |  | 114–116 |
| p-chlorophenyl |  | 102–105 |
| p-trifluoromethylphenyl |  | 108–111 |
| o-methylphenyl |  | 94–98 |
| m-methoxyphenyl | IR (film) | 1752, 1723, 1660 cm$^{-1}$ |
| 2,4-dichlorophenyl |  | 116–118 |
| 2,6-dichlorophenyl |  | 130–131 |
| o-fluorophenyl |  | 109–110 |

(d) The hexahydro-carboxylate used as the starting material in paragraph 1(c) can, in turn, be prepared as follows:

150 g of 5-(o-chlorophenyl)-2-piperidone are dissolved in 2 liters of methylene chloride and added dropwise at room temperature while stirring within 60 minutes to 410 g of triethyloxonium tetrafluoroborate (Merrwein salt) in 1 liter of methylene chloride. Subsequently, the mixture is boiled at reflux for 4 hours and left at room temperature for a further 15 hours. 372g of potassium carbonate in 370 ml. of water are then added dropwise to the solution which is cooled to 0° C., the mixture being stirred intensively. The mixture is stirred at room temperature for a further 2 hours, the methylene chloride phase is subsequently decanted off and the residue is extracted with two 500 ml. portions of methylene chloride. The methylene chloride phase, dried over potassium carbonate, is concentrated to an oily, partially crystalline residue, then boiled up in 1 liter of hexane and filtered while hot. From the filtrate there are obtained, after evaporation of the hexane, 151.4 g of the oily lactim ether, namely, 3-(o-chlorophenyl)-6-ethoxy-2,3,4,5-tetrahydropyridine [IR (film): 1684 cm$^{-1}$].

The lactim ether (151.4 g) is dissolved in 1.4 liters of methanol, 1.3 g of anhydrous p-toluenesulfonic acid are added thereto and 85 g of 3-oxo-5-pentenoic acid methyl ester (Nazarov reagent) are added within 60 minutes. After 20 hours at room temperature, the readily volatile constituents are removed in vacuo and the residue is subsequently taken up in methylene chloride and washed with 500 ml. of saturated sodium carbonate solution. The methylene chloride phase, dried over magnesium sulfate, is concentrated and the residue is crystallized from 800 ml of ethyl acetate/ether (4:1). There are obtained 123.7 g (54%) of methyl rac-7-(o-chlorophenyl)-3,4,6,7,8,9-hexahydro-2-oxo-2H-quinolizine-1-carboxylate having a melting point of 145°–147° C.

When in place of 5-(o-chlorophenyl)-2-piperidone equivalent amounts of corresponding substituted piperidones are used, the following compounds are obtained:

TABLE 5

Methyl rac-7-(R$_a$)-3,4,6,7,8,9-hexahydro-2-oxo-2H-quinolizine-1-carboxylate:

|  | M.p. ° C. |
|---|---|
| R$_a$ = phenyl | 148–149 |
| p-chlorophenyl | 185–187 |
| p-trifluoromethylphenyl | 144–145 |
| o-methylphenyl | 183–184 |
| m-methoxyphenyl | 133–134 |
| 2,4-dichlorophenyl | 153–155 |
| 2,6-dichlorophenyl | 159–162 |
| o-fluorophenyl | 165–167 |

EXAMPLE 2

A solution of 12.2 g of rac-(9aβH)-2α-tert.butyl-7β-(2,4-dichlorophenyl)octahydro-2-H-quinolizin-2-ol in 80 ml of methanol is treated with a solution of 13.3 g of (+)-2,2'-(1,1'-binaphthyl)-phosphoric acid in 250 ml of methanol and 250 ml of methylene chloride. The separated jelly is brought into solution with 1.2 liters of hot methanol and subsequently evaporated to a volume of 500 ml, the (+)-phosphate crystallizing out at 0° C.; 8.7 g (72.5%); be liberated with ammonia the (+)-base [(+) (2R, 7S, 9aS)-2-tert.butyl-7-(2,4-dichlorophenyl)octahydro-2H-quinolizin-2-ol] (4.2 g) which, dissolved in 50 ml of ethanol and treated with 2.5 ml of 5N hydrochloric acid in ethanol at 0° C., yields 4.0 g of (+)-hydrochloride salt; melting point 275°–276° C.; [α]$_D$ = +23.1° (c=1% in methanol).

The mother liquor from the crystallization of the (+)-phosphate is made basic with concentrated ammonia and extracted with ethyl acetate/ether (1:1). The organic phase is washed neutral with water, dried over magnesium sulfate and evaporated, 7.7 g of base being obtained. This base is brought into solution with 50 ml of methanol and 7.33 g of (−)-2,2'-(1,1'-binaphthyl)-phosphoric acid in 200 ml of methanol and 200 ml of methylene chloride are added. The mixture is then concentrated to 250 ml, 250 ml of acetone are added and the mixture is cooled to 0° C. 8.2 g of (−)-phosphate crystallize out; melting point 279°–281° C. The base [(−)(2S, 7R, 9aR)-2-tert.butyl-7-(2,4-dichlorophenyl)octahydro-2H-quinolizin-2-ol] (4.2 g) liberated therefrom with ammonia is dissolved in 50 ml of ethanol and treated with 2.5 ml of 5 N hydrochloric acid in ethanol. At 0° C. there crystallize out 4.1 g of (−)-hydrochloride salt; melting point 275°–276° C.; [α]$_D$=23.1° (c=1% in methanol).

The following enantiomers can be isolated in an analogous manner by cleavage of the corresponding racemates:

(+)-2-Butyloctahydro-7-phenyl-2-H-quinolizin-2-ol; base melting point 99°–101° C., and (−)-2-butyloctahydro-7-phenyl-2H-quinolizin-2-ol; base melting point 99°–101° C.

EXAMPLE 3

From 0.54 g. of magnesium shavings in 5 ml. of absolute ether and 5 g. of m-bromobenzotrifluoride in 10 ml. of ether there is first prepared a Grignard reagent by boiling under reflux for 2 hours. To the suspension, cooled to 0° C., there are subsequently added dropwise 2.64 g. of rac-(9aβH)-7β-(p-chlorophenyl)octahydro- 2H-quinolizin-2-one [prepared according to Example 1(b)] in 25 ml. of absolute ether, and the mixture is stirred for a further hour at room temperature under argon. For the hydrolysis, the mixture is treated with saturated ammonium chloride solution and the product is extracted with methylene chloride. The organic phase, washed with saturated sodium chloride solution, is dried over magnesium sulfate and evaporated, there being obtained a residue weighing 4.60 g. After chromatography on silica gel with ethyl acetate/methanol, this residue gives two diasteromeric products, namely:

1.4 g. of rac-(9aβH)-2α-(m-trifluoromethylphenyl)-7β-(p-chlorophenyl)octahydro-2H-quinolizin-2-ol having a melting point of 119°–123° C. (34%), and 1.2 g of rac-(9aβH)-2β-(m-trifluoromethylphenyl)-7β-(p-chlorophenyl)octahydro-2H-quinolizin-2-ol having a melting point of 122°–124° C. (29%).

When equimolar amounts of analogous alkyl- or aryllithium reagents are used, the compounds listed in Example 1a, Table 2 can be obtained.

EXAMPLE 4

20.0 g of rac.-(9aβH)-2α-tert.butyl-7β-(o-chlorophenyl)octahydro-2H-quinolizin-2-ol [prepared according to Example 1(a)] are dissolved in 130 ml. of isopropenyl acetate and 11.7 g. of anhydrous p-toluenesulfonic acid are added. The mixture is then boiled at reflux under argon for 1 hour while stirring. After cooling the solution, a further 20 ml. of ether are added. The solution is left to stand for 2 hours and then the separated p-toluenesulfonate of the product is filtered off and dried, 22.5 g. being obtained. The base [rac-(9aβH)-2α-tert.butyl-7β-(o-chlorophenyl)octahydro-2-H-quinolizin-2-yl acetate] can be liberated from the p-toluenesulfonate with sodium bicarbonate solution. The yield is 15.8 g. and the hydrochloride salt melts at 241°–242° C.

When equimolar amounts of the alkylcarbinols listed in Example 1(a) are used in the reaction, the acetates mentioned in Table 6 are obtained:

TABLE 6 rac-(9aβ H)-2α-(R$_b$)-7 β-(R$_a$)octahydro-2H-quinolizin-2-yl acetate:

| | | | M.p. °C. |
|---|---|---|---|
| R$_b$ = tert.butyl | R$_a$ = phenyl | HCl salt | 247–248 |
| " | p-chlorophenyl | " | 244–246 |
| " | 2,4-dichlorophenyl | " | 246–247 |
| n-butyl | phenyl | " | 248–250 |

(+)-(2-Butyloctahydro-7-phenyl-2H-quinolizin-2-yl acetate) HCl, melting point 242°–243° C.;

(−)-(2-butyloctahydro-7-phenyl-2H-quinolizin-2-yl acetate) HCl, melting point 242°–243° C.

EXAMPLE 5

5.0 g. of rac-(9aβH)-2α-tert.butyl-(o-chlorophenyl)octahydro-2H-quinolizin-2-ol are dissolved in 20 ml. of pyridine and treated dropwise at room temperature within 15 minutes with 20 ml. of trifluoroacetic acid anhydride. After 22 hours at room temperature, the solution is evaporated in vacuo and the residue is dissolved in 50 ml. of toluene and concentrated. Subsequently, the oily residue is chromatographed on 100 g. of silica gel with ethyl acetate. The eluate yields 5.4 g. of the product base [rac-(9aβH)-2α-tert.butyl-7β-(o-chlorophenyl)octahydro-2H-quinolizin-2-yl trifluoroacetate]. The hydrochloride salt melts at 172°–273° C.

When equimolar amounts of the alkyl- or arylcarbinols listed in Examples 1(a) and 3 are used for the reaction, the trifluoroacetates listed in Table 7 can be obtained:

TABLE 7 rac-(9aβH)-R$_b$)-7β-(R$_a$)octahydro-αH-quinolizin-2-yl trifluoroacetate:

| | | | M.p. °C. |
|---|---|---|---|
| R$_b$ = 2α-tert.butyl | R$_a$ = phenyl | HCl salt | 170–172 |
| 2α-phenyl | phenyl | " | 164–166 |

When in place of trifluoroacetic acid anhydride equimolar amounts of the alkyl- or arylcarbinols listed in Examples 1(a) and 3 are reacted with analogous carboxylic acid anhydrides, the following carbinol acylates can be obtained:

TABLE 8 rac-(9aβH)-R$_b$)-7β-(R$_a$)octahydro-2H-quinolizin-2-yl-(R$_c$):

| | | | | M.p. °C. |
|---|---|---|---|---|
| R$_b$ = 2α-phenyl | R$_a$ = o-chlorophenyl | C = acetate | HCl salt | 220–222 |
| 2β-phenyl | R$_a$ = o-chlorophenyl | " | HCl salt | 218–220 |
| 2α-phenyl | phenyl | propionate | HCl salt | 242–243 |
| 2α-phenyl | m-methoxyphenyl | " | HCl salt | 212–214 |
| 2β-phenyl | m-methoxyphenyl | " | HCl salt | 233–235 |
| 2α-m-methoxyphenyl | phenyl | " | HCl salt | 233–234 |
| 2β-phenyl | " | " | oxalate | 120–122 |

EXAMPLE 6

(a) 3.0 g. of rac-(9aβH)-2β-phenyl-7β-(o-chlorophenyl)-octahydro-2H-quinolizin-2-ol [prepared according to Example 1(a)] are dissolved in 75 ml. of methanol, treated within 15 minutes with 15 ml. of concentrated sulfuric acid and then boiled at reflux for 2 hours. The cooled solution is poured on to concentrated sodium hydroxide/ice and extracted with three 200 ml. portions of ethyl acetate. The organic phase, dried over magnesium sulfate, gives, after concentration, 3.2 g. of crude product which is chromatographed on 300 g. of silica gel with hexane/ether. There are obtained 1.7 g. of rac-(9aβH)-2β-methoxy-2-phenyl-7β-(o-chlorophenyl)octahydro-2-H-quinolizine. The hydrochloride salt melts at 258°–260° C.

When in place of rac-(9aβH)-2β-phenyl-7β-(o-chlorophenyl)octahydro-2H-quinolizin-2-ol corresponding substituted arylcarbinols are reacted with C$_1$–C$_4$-alcohols, there are obtained the following O—(C$_1$–C$_4$)-alkyl compounds:

TABLE 9 rac-(9aβH)-2β-(R$_b$)-2-phenyl-7β-(R$_a$)octahydro-2H-quinolizine:

| | | | M.p. °C. |
|---|---|---|---|
| R$_b$ = methoxy | R$_a$ = phenyl | HCl salt | 277–279 |
| ethoxy | " | " | 254–255 |

(b) 0.5 g. of rac-(9aβH)-2α-phenyl-7β-(o-chlorophenyl)octahydro-2H-quinolizin-2-ol [prepared according to Example 1(a)] are dissolved in 5 ml. of HMPA (hexamethylphosphoric acid triamide) and treated at 0° C. with 0.1 g. of sodium hydride (50–60% in mineral oil). The mixture is stirred for 0.5 hour at 0° C. and then 0.2 ml. of methyl iodide is added thereto. Subsequently, the mixture is stirred at room temperature for 15 hours. For the working-up, the mixture is poured into 50 ml. of water and extracted with two 50 ml. portions of ethyl acetate. The ethyl acetate phase is washed with three 50 ml. portions of water, dried over magnesium sulfate and evaporated. Chromatography on 50 g. of silica gel with hexane/ether gives 0.2 g. of rac-(9aβH)-2β-methoxy-2-phenyl-7β-(o-chlorophenyl)octahydro-2H-quinolizine. The hydrochloride salt melts at 258°–260° C.

EXAMPLE 7

(a) A solution of 7.45 g. of rac-1-[7β-(o-chlorophenyl)-3,6,7,8,9,9aβ-hexahydro-4H-quinolizin-2-yl]-5,6-dimethyl-2-benzimidazoline in 30 ml. of concentrated sulfuric acid and 300 ml. of absolute ethanol is hydrogenated at room temperature with 0.40 g. of platinum oxide for 6 hours. Subsequently, the catalyst is filtered off, the filtrate is evaporated and the residue is partitioned between chloroform and 2 N sodium hydroxide. The chloroform phase, dried over potassium carbonate, gives, after evaporation, 7.5 g. of crude product. For the purification, the hydrochloride salt is crystallized from methanol/ether, there being obtained 6.7 g. of rac-1-[(9aβH)-7β-(o-chlorophenyl)octahydro-2H-quinolizin-2α-yl]-5,6-dimethyl-2-benzimidazolinone hydrochloride having a melting point of 310° C. An alternative purification comprises chromatographing the base on silica gel with methylene chloride/methanol. The melting point of the base is 268°–272° C.

When in place of rac-1-[7β-(o-chlorophenyl)-3,6,7,8,9,9aβ-hexahydro-4H-quinolizin-2α-yl]-5,6-dimethyl-2-benzimidazolinone equimolar amounts of corresponding substituted educts are hydrogenated with the catalysts listed in Table 10, the following products are obtained:

TABLE 10 rac-1-[(9aβH)-7β-(R$_a$)octahydro-2H-quinolizin-2α-yl]-(B)-2-benzimidazolinone:

| R$_a$ = | B = | Catalyst: | | M.p. °C. |
|---|---|---|---|---|
| o-chlorophenyl | 5,6-dichloro | PtO$_2$ | HCl salt | 300–305 |
| o-chlorophenyl | 5,6-H | PtO$_2$ | " | 315–318 |
| o-chlorophenyl | 5,6-dimethoxy | PtO$_2$ | " | 229–235 |
| o-chlorophenyl | 5-(CH$_2$)$_4$-6 | PtO$_2$ | " | 245–250 |
| p-chlorophenyl | 5,6-H | PtO$_2$ | base | 244–248 |
| p-chlorophenyl | 5,6-dimethyl | PtO$_2$ | " | 289–295 |
| o-methylphenyl | 5,6-H | 10% Pd/C | HCl salt | 285–290 |
| o-methylphenyl | 5,6-dimethyl | 10% Pd/C | " | 291–293 |
| o-methylphenyl | 5,6-dichloro | PtO$_2$ | base | 294–297 |
| phenyl | 5,6-H | 10% Pd/C | HCl salt | 223–228 |
| " | 5,6-dimethyl | 10% Pd/C | " | 295–302 |
| " | 5,6-dichloro | PtO$_2$ | base | 295–300 |
| " | 5,6-dimethoxy | 10% Pd/C | " | 248–250 |
| o-fluorophenyl | 5,6-dimethyl | 10% Pd/C | HCl salt | >300 |
| o-fluorophenyl | 5,6-dichloro | PtO$_2$ | " | >250 |
| o-fluorophenyl | 5,6-difluoro | PtO$_2$ | " | >300 |
| o-fluoro- | 5-(CH$_2$)$_4$-6 | PtO$_2$ | " | 248–250 |

TABLE 10-continued rac-1-[(9aβH)-7β-(R$_a$)octahydro-2H-quinolizin-2α-yl]-(B)-2-benzimidazolinone:

| | | Catalyst: | | M.p. °C. |
|---|---|---|---|---|
| phenyl | | | | |

(b) The rac-1-[7β-(o-chlorophenyl)-3,6,7,8,9,9aβ-hexahydro-4H-quinolizin-2-yl]-5,6-dimethyl-2-benzimidazolinone used as the starting material can be prepared as follows:

6.35 g. of 4,5-dimethyl-1,2-phenylenediamine are dissolved in 100 ml. of xylene, heated to reflux and there are added within 2 hours 15 g. of methyl rac-(1αH,9aβH)-7β-(o-chlorophenyl)octahydro-2-oxo-2H-quinolizine-1-caboxylate [prepared according to Example 1(c)] in 100 ml. of xylene. The mixture is then boiled under reflux for 7 hours and subsequently cooled down. From the solution there crystallize out 13.65 g. of rac-1-[7β-(o-chlorophenyl)-3,6,7,8,9,9aβ-hexahydro-4H-quinolizin-2-yl]-5,6-dimethyl-2-benzimidazolinone having a melting point of 239°–241° C.

When in place of methyl rac-(1αH,9aβH)-7β-(o-chlorophenyl)octahydro-2-oxo-2H-quinolizine-1-carboxylate equimolar amounts of corresponding substituted β-keto-esters are reacted with 1,2-phenylene-diamines the following compounds are obtained:

TABLE 11 rac-1-[7β-(R$_a$)-3,6,7,8,9,9aβ-hexahydro-4H-quinolizine-2-yl]-(B)-2-benzimidazolinone:

| R$_a$ = | B = | | M.p. °C. |
|---|---|---|---|
| o-chloro- | 5,6-dichloro | HCl salt | 281–284 |
| " | 5,6-H | " | 267–269 |
| " | 5,6-dimethoxy | " | 225 (dec.) |
| " | 5-(CH$_2$)$_4$-6 | base | 246–249 |
| p-chlorophenyl | 5,6-H | HCl salt | 274–277 |
| p-chlorophenyl | 5,6-dimethyl | " | 228–230 |
| o-methylphenyl | 5,6-H | " | 277–279 |
| o-methylphenyl | 5,6-dimethyl | " | 226–230 |
| o-methylphenyl | 5,6-dichloro | " | 286–289 |
| phenyl | 5,6-dimethyl | base | 259–262 |
| " | 5,6-dichloro | " | 293–296 |
| " | 5,6-dimethoxy | " | 241–243 |
| 2'-methoxy-5'-chloro-phenyl | 5,6-dimethyl | " | 248–251 |
| o-fluorophenyl | 5,6-dimethyl | " | 260–263 |
| o-fluorophenyl | 5,6-dichloro | " | 298–302 |
| o-fluorophenyl | 5,6-difluoro | " | 257–259 |
| o-fluorophenyl | 5-(CH$_2$)$_4$-6 | " | 238–241 |

EXAMPLE 8

3.0 g. of rac-1-[(9aβH)-7β-(o-chlorophenyl)octahydro-2H-quinolizin-2α-yl]-2-benzimidazolinone [prepared according to Example 7(a)] are suspended in 30 ml. of dry monoglyme, treated with 0.41 g. of sodium hydride (50–60% in mineral oil) and stirred at room temperature for 1 hour. Subsequently, the mixture is cooled to 0° C. and 1.23 g. of methyl iodide are added. After 30 minutes at room temperature, the mixture is poured into 50 ml. of water and extracted with ethyl acetate. The organic phase, dried over magnesium sulfate, is concentrated and the crude product is chromatographed on silica gel with methylene chloride/methanol. There are obtained 2.10 g. of rac-1-[(9aβH)-7β-(o-chlorophenyl)octahydro-2H-quinolizin-2α-yl]-3-methyl-2-benzimidazolinone. The hydrochloride salt melts at 315°–320° C.

EXAMPLE 9

0.5 g. of rac-1-[(9aβH)-7β-(o-chlorophenyl)octahydro-2H-quinolizin-2α-yl]-5,6-dimethyl-2-benzimidazolinone [prepared according to Example 7(a)] is heated to 150° C. for 3 hours with 1.0 g. of phosphorus pentasulfide in 5 ml. of pyridine. The mixture is then evaporated and the residue is partitioned between 2 N sodium hydroxide and chloroform/isopropanol. The organic phase is washed with saturated sodium chloride solution, dried over magnesium sulfate and evaporated. Chromatography of the crude product on silica gel with methylene chloride/methanol gives 0.22 g. of rac-1-[(9aβH)-7β-(o-chlorophenyl)octahydro-2H-quinolizin-2α-yl]-5,6-dimethyl-2-benzimidazolinethione having a melting point of 293°–297° C.

EXAMPLE 10

(a) A solution of 7.20 g. of rac-(9aβH)-7β-(o-fluorophenyl)octahydro-2α-(α',α',α'-trifluoro-2-amino-p-toluidino)-2H-quinolizine in 180 ml. of methylene chloride is treated with 4.59 g. of 93% N,N'-carbonyldiimidazole and the mixture is stirred at room temperature overnight. The separated product is filtered off after 20 hours, washed with three 100 ml. portions of methylene chloride and subsequently dried. There are obtained 6.45 g. of crystalline rac-1-[(9aβH)-7β-(o-fluorophenyl)octahydro-2H-quinolizin-2α-yl]-5-(trifluoromethyl)-2-benzimidazolinone having a melting point of 304°–306° C.

When in place of rac-(9aβH)-7β-(o-fluorophenyl)octahydro-2α-(α',α',α'-trifluoro-2-amino-p-toluidino)-2H-quinolizine corresponding substituted phenylene-diamines are reacted with N,N'-carbonyldiimidazole, the following compounds are obtained:

TABLE 12

| rac-1-[(9aβ H)-7β-(R<sub>a</sub>)octahydro-2H-quinolizin-2α-yl]-(B)-2-benzimidazolinone: | | |
|---|---|---|
| | | M.p. °C. |
| R<sub>a</sub> = o-fluorophenyl | B = 5-chloro | 283–285 (base); 298–304 (HCl salt) |
| o-chlorophenyl | 5-chloro | 223–230 (base) |
| o-chlorophenyl | 5-trifluoromethyl | 257–259 (base); 240–245 (HCl salt) |
| o-chlorophenyl | 5,6-dichloro | 300–305 (HCl salt) |
| o-fluorophenyl | 5,6-dichloro | >250 (HCl salt) |

(b) The rac-(9aβH)-7β-(o-fluorophenyl)octahydro-2α-(α',α',α'-trifluoro-2-amino-p-toluidino)-2H-quinolizine used as the starting material in paragraph (a) of this Example can be prepared as follows:

25.7 g. of rac-(9aβH)-7β-(o-fluorophenyl)octahydro-2α-(α',α',α'-trifluoro-2-nitro-p-toluidino)-2H-quinolizine are hydrogenated in 0.9 liter of tetrahydrofuran and 0.9 liter of methanol with 13 g. of Raney nickel for 20 hours at room temperature and atmospheric pressure. The catalyst is then removed by suction filtration and the filtrate is evaporated. There are obtained 23.6 g. of crystalline rac-(9aβH)-7β-(o-fluorophenyl)octahydro-2α-(α',α',α'-trifluoro-2-amino-p-toluidino)-2H-quinolizine which, if desired, can be recrystallized from alcohol/ethyl acetate; melting point 133°–138°.

If in place of rac-(9aβH)-7β-(o-fluorophenyl)octahydro-2α-(α',α',α'-trifluoro-2-nitro-p-toluidino)-2H-quinolizine corresponding substituted nitro compounds are reduced, the following compounds are obtained:

TABLE 13

| rac-(9aβH)-7β-(R<sub>a</sub>)octahydro-2α-(B)-2H-quinolizine: | | |
|---|---|---|
| | | M.p. °C. |
| R<sub>a</sub> = o-fluorophenyl | B = 2-amino-4-chloro-anilino | 137–141 |
| o-fluorophenyl | 2-amino-4,5-dichloro-anilino | 164–166 |
| o-chlorophenyl | 2-amino-4-chloro-anilino | 170–172 |
| o-chlorophenyl | 2-amino-4,5-dichloro-anilino | 148–150 |
| o-chlorophenyl | α', α', α'-trifluoro-2-amino-p-toluidino | 151–153 |

(c) The rac-(9aβH)-7β-(o-fluorophenyl)octahydro-2α-(α',α',α'-trifluoro-2-nitro-p-toluidino)-2H-quinolizine used as the starting material in paragraph (b) of this Example can be prepared as follows:

20.0 g. of rac-(9aβH)-7β-(o-fluorophenyl)-2α-(amino)-octahydro-2H-quinolizine are dissolved in 300 ml. of cyclohexanol having a purity above 99%, treated with 8.62 g. of anhydrous sodium carbonate and heated to 160° C. At this temperature there is added dropwise within 3 hours a solution of 20.0 g. of 4-chloro-3-nitro-benzotrifluoride in 200 ml. of cyclohexanol having a purity above 99%. The solution is then held at 160° C. for a further 4 hours. After cooling to room temperature, inorganic solids are filtered off and the filtrate is evaporated in vacuo. The residue is dissolved in 500 ml. of hot ethyl acetate, 5 g. of active carbon are added to the solution and the mixture is boiled at reflux for 5 minutes. The mixture is then filtered while hot through Hyflo Super Cel, the filtrate is concentrated to 200 ml. and 100 ml. of n-hexane are added. There crystallize 22.3 g. of rac-(9aβH)-7β-(o-fluorophenyl)octahydro-2α-(α',α',α'-trifluoro-2-nitro-p-toluidino)-2H-quinolizine having a melting point of 163°–165° C. By chromatography of the mother liquor on 250 g. of silica gel with n-hexane/ethyl acetate (4:1) there are obtained a further 5.45 g. of product. The total yield is 78.8%.

Where in place of rac-(9aβH)-7β-(o-fluorophenyl)-2α-(amino)octahydro-2H-quinolizine corresponding substituted amino-quinolizidines are reacted with corresponding substituted o-chloro-nitrobenzenes, the following compounds are obtained:

TABLE 14

| rac-(9aβH)-7β-(R<sub>a</sub>)octahydro-2α-(B)-2H-quinolizine: | | |
|---|---|---|
| | | M.p. °C. |
| R<sub>a</sub> = o-fluorophenyl | B = 2-nitro-4-chloro-anilino | 185–187 |
| o-fluorophenyl | 2-nitro-4,5-dichloro-anilino | 202–203 |
| o-chlorophenyl | 2-nitro-4-chloro-anilino | 183–185 |
| o-chlorophenyl | 2-nitro-4,5-dichloro-anilino | 197–199 |
| o-chlorophenyl | α',α',α'-trifluoro-2-nitro-p-toluidino | 154–155 |

(d) The rac-(9aβH)-7β-(o-fluorophenyl)-2α-(amino)octahydro-2H-quinolizine used as the starting material in paragraph (c) can be prepared as follows:

84.3 g. of rac-(9aβH)-7β-(o-fluorophenyl)octahydro-2H-quinolizin-2-one [see Example 1(b), Table 3] are heated at reflux for 1.5 hours in 1700 ml. of methanol with 47.4 g. of hydroxylamine hydrochloride and 94.3 g. of anhydrous potassium carbonate. The methanol is subsequently distilled off and the residue is partitioned between 750 ml. of water, 600 ml. of chloroform and 150 ml. of isopropanol. The aqueous phase is back-extracted twice with in each case 250 ml. of a mixture of 200 ml. of chloroform and 50 ml. of isopropanol, the combined organic phases are dried over magnesium sulfate and then evaporated. There are obtained 85.3 g. of oxime which is dissolved in 1.5 liters of tetrahydrofuran, 0.5 liter of alcohol and 1 liter of 5% (g/g) ammonia in alcohol and hydrogenated with 45 g. of Raney nickel for 30 hours at room temperature and atmospheric pressure. The catalyst is then filtered off and the filtrate is evaporated. From the residue there can be crystallized by dissolution in 400 ml. of alcohol and addition of 130 ml. of 5 N hydrogen chloride in alcohol 53.5 g. of the dihydrochloride salt of rac-(9aβH)-7β-(o-fluorophenyl)-2α-(amino)octahydro-2H-quinolizine having a melting point of 299°–302° C. The diastereomeric rac-(9aβH)-7β-(o-fluorophenyl)-2β-(amino)octahydro-2H-quinolizine is dissolved as the dihydrochloride in the mother liquor.

When in place of rac-(9aβH)-7β(o-fluorophenyl)octahydro-2H-quinolizin-21-one the corresponding substituted quinolizidinone is aminated, there is obtained the following compound:

TABLE 15

| rac-(9aβH)-7β-(R$_a$)-2α-(amino)octahydro-2H-quinolizine: | |
|---|---|
| | M.p. °C. |
| R$_a$ = o-chlorophenyl | 293–296 (2 HCl) |

EXAMPLE 11

A solution of 7.20 g. of rac-(9aβH)-7β-(o-fluorophenyl)octahydro-2α-(α',α',α'-trifluoro-2-amino-p-toluidino)-2H-quinolizine [prepared according to Example 10(b)] in 180 ml. of methylene chloride is treated with 4.75 g. of N,N'-thiocarbonyldimidazole and the mixture is stirred at room temperature overnight. After 20 hours, the separated product is filtered off, washed with two 100 ml. portions of methylene chloride and subsequently dried. There are obtained 5.80 g. of crystalline rac-1-[(9aβH)-7β-(o-fluorophenyl)octahydro-2H-quinolizin-2α-yl]-5-(trifluoromethyl)-2-benzimidazolinthione having a melting point of 308°–309° C.

When in place of rac-(9aβH)-7β-(o-fluorophenyl)octahydro-2α-(α',α',α'-trifluoro-2-amino-p-toluidino)-2H-quinolizine corresponding substituted phenylene-diamines are reacted with N,N-thiocarbonyldiimidazole, the following compounds are obtained:

TABLE 16

| rac-1-[(9aβH)-7β-(R$_a$)octahydro-2H-quinolizin-2α-yl]-(B)-2-benzimidazolinthione: | | | |
|---|---|---|---|
| | | | M.p. °C. |
| R$_a$ = | o-fluorophenyl | B = 5-chloro | >300 |
| | o-fluorophenyl | 5,6-dichloro | >310 |
| | o-chlorophenyl | 5-chloro | 264–267 |
| | o-chlorophenyl | 5,6-dichloro | >295 |

EXAMPLE 12

A solution of 5.80 g. of rac-(9aβH)-2α-(2-amino-4,5-dichloro-anilino)-7β-(o-chlorophenyl)octahydro-2H-quinolizine [see Example 10(b)] in 60 ml. of m-xylene is boiled at reflux for 6 hours with 20 ml. of triethyl orthoacetate. The solution is cooled down, poured into cold 2 N sodium hydroxide and extracted twice with 300 ml. of methylene chloride each time. The organic phase, dried over anhydrous sodium carbonate, is subsequently evaporated. The residue is dissolved in 50 ml. of 5 N hydrochloric acid in alcohol and heated to reflux for 1 hour. The separated dihydrochloride of the product is filtered off and dried. There are obtained 5.60 g. of the dihydrochloride salt of rac-(9aβH)-7β-(o-chlorophenyl)-2α-(5,6-dichloro-2-methyl-1-benzimidazolyl)octahydro-2H-quinolizine having a melting point of 231°–236° C. The yield is 77%.

Where in place of rac-(9aβH)-2α-(2-amino-4,5-dichloroanilino)-7β-(o-chlorophenyl)octahydro-2H-quinolizine the corresponding substituted phenylenediamine is reacted with triethyl orthoacetate, the following compound can be obtained:

TABLE 17

| rac-(9aβH)-7β-(R$_a$)-2α-[(B)-2-methyl-1-benzimidazolyl]octahydro-2H-quinolizine 2 HCl: | | |
|---|---|---|
| | | M.p. °C. |
| R$_a$ = o-chlorophenyl | B = 5-chloro | 240–245 |

EXAMPLE 13

2.70 g. of a 1:1 mixture of rac-(9aβH)-2-phenyl-7β-(o-chlorophenyl)-3,4,6,7,8,9-hexahydro-2H-quinolizine and rac-(9aβH)-2-phenyl-7β-(o-chorophenyl)-1,4,6,7,8,9-hexahydro-2H-quinolizine are boiled under reflux for 15 hours with 70 ml. of water and 14 ml. of 98% sulfuric acid. The solution is cooled down, poured into a saturated aqueous potassium carbonate solution, diluted with 200 ml. of water and extracted with three 200 ml. portions of ethyl acetate. The combined ethyl acetate extracts are dried over magnesium sulfate and evaporated. The crude product (2.35 g.) is chromatographed over 100 g. of silica gel using ethyl acetate for the elution. 1.55 g. of educt mixture are recovered in a first fraction and from a further fraction there can be obtained 0.15 g. (yield 3.5%) of rac-(9aβH)-2α-phenyl-7β-(o-chlorophenyl)octahydro-2-H-quinolizin-2-ol. The hydrochloride salt melts at 265°–275° C.

The double-bond isomer mixture used as the starting material can be obtained as follows:

5.00 g. of rac-(9aβH)-2β-phenyl-7β-(o-chlorophenyl)octahydro-2H-quinolizin-2-ol [see Example 1(a), Table 2] are dissolved in 25 ml. of pyridine and 2.1 ml. of thionyl chloride are added. After standing at room temperature for 2 hours, the mixture is evaporated in vacuo and subsequently partitioned between chloroform and water. The organic phase, dried over magnesium sulfate, is evaporated and the crude product (3.90 g.) is filered with ethyl acetate over 200 g. of aluminum oxide (activity III). In this manner there can be eluted 2.75 g. of a 1:1 mixture of rac-(9aβH)-2-phenyl-7β-(o-chlorophenyl)-3,4,6,7,8,9-hexahydro-2H-quinolizine and rac-(9aβH)-2-phenyl-7β-(o-chlorophenyl)-1,4,6,7,8,9-hexahydro-2H-quinolizine; NMR (CDCl$_3$): 5.93+6.08 ppm (in each case 2 broad singlets in the ratio 1:1, together 1 proton).

EXAMPLE 14

0.068 g. of sodium hydride (50% in mineral oil), suspended in 10 ml, of 1,2-dimethoxyethane, is treated with 0.160 g. of benzimidazolinone and subsequently with 0.500 g. of a 1:1 mixture of rac-(9aβH)-7β-(o-chlorophenyl)-octahydro-2H-quinolizin-2α-yl p-toluenesulfonate and rac-(9aβH)-7β-(o-chlorophenyl)octahydro-2H-quinolizin-2β-yl p-toluenesulfonate in 10 ml. of 1,2-dimethoxyethane and the mixture is then heated to reflux for 45 hours. After cooling, the mixture is partitioned between chloroform and water, the organic phase is dried over magnesium sulfate and evaporated. The resulting crude product (0.450 g.) is chromatographed on 50 g. of silica gel using chloroform containing 1% methanol for the elution, there being obtained 0.040 g. (9% yield) of rac-1-[(9aβH)-7β-(o-chlorophenyl)octahydro-2H-quinolizin-2α-yl]-2-benzimidazolinone. The hydrochloride salt melts at 315°–317° C.

The 1:1 mixture of diastereomeric p-toluenesulfonates used as the starting material can be prepared as follows:

5.00 g. of rac-(9aβH)-7β-(o-chlorophenyl)-octahydro-2H-quinolizin-2-one [see Example 1(b)] in 50 ml. of methanol are treated with 0.7 g. of sodium borohydride and stirred at room temperature for 45 minutes. Subsequently, the mixture is partitioned between water and ethyl acetate, the organic phase is dried over magnesium sulfate and concentrated. The crude product obtained is chromatographed over 200 g. of silica gel with diethyl ether and the eluate is evaporated, there being obtained 5.0 g. of a mixture of diastereomeric alcohols. The mixture of the alcohols is dissolved in 50 ml. of pyridine and 7.3 g. of p-toluenesulfonic acid chloride are added thereto. After stirring at room temperature for 2 hours, the mixture is evaporated, the residue is partitioned between 2 N sodium hydroxide and ethyl acetate and, after drying, the organic phase is concentrated. By chromatography on 100 g. of silica gel with methylene chloride containing 1% methanol there can be obtained 2.20 g. of 1:1 mixture of rac-(9aβH)-7β-(o-chlorophenyl)octahydro-2H-quinolizin-2β-yl p-toluenesulfonate and rac-(9aβH)-7β-(o-chlorophenyl)octahydro-2H-quinolizin-2α-yl p-toluenesulfonate [NMR (CDCl₃): 2 singlets 2.33+2.43 ppm] as well as 5.80 g. of rac-(9aβH)-7β-(o-chlorophenyl)octahydro-2H-quinolizin-2α-yl p-toluenesulfonate [NMR (CDCl₃): 1 singlet 2.43 ppm].

The following Examples illustrate pharmaceutical preparations containing the phenyl-quinolizidines provided by the present invention:

EXAMPLE A

| Tablets | Per Tablet |
| --- | --- |
| (−)-(2S,7R,9aR)-2-Tert.butyl-7-(2,4-dichlorophenyl)octahydro-2H-quinolizin-2-ol HCl | 100 mg. |
| Lactose | 202 mg. |
| Maize starch | 80 mg. |
| Hydrolyzed maize starch | 20 mg. |
| Calcium stearate | 8 mg. |
| Total Weight | 410 mg. |

The (−)-(2S,7R,9aR)-2-tert. butyl-7-(2,4-dichlorophenyl)octahydro-2H-quinolizin-2-ol hydrochloride, the lactose, the maize starch and the hydrolyzed maize starch are mixed and granulated with water to a viscous paste. This paste is passed through a sieve and subsequently dried overnight at 45° C. The dried granulate is passed through a sieve and subsequently mixed with calcium stearate. The resulting mixture is pressed to tablets weighing 410 mg. and having a diameter of about 10 mm.

EXAMPLE B

| Tablets | Per Tablet |
| --- | --- |
| (+)-2-Butyloctahydro-7-phenyl-2H-quinolizin-2-yl acetate HCl | 10.0 mg. |
| Lactose | 129.0 mg. |
| Maize starch | 50.0 mg. |
| Gelatinized maize starch | 8.0 mg. |
| Calcium stearate | 3.0 mg. |
| Total Weight | 200.0 mg. |

The (+)-2-butyloctahydro-7-phenyl-2H-quinolizin-2-yl acetate hydrochloride, the lactose, the maize starch and the gelatinized maize starch are intimately mixed with one another. The mixture is passed through a comminuting machine and subsequently moistened with water to a thick paste. The moist mass is passed through a sieve. The moist granulate is dried at 45° C. The dried granulate is mixed thoroughly with the calcium stearate. The granulate is now pressed to tablets weighing 200 mg. and having a diameter of about 8 mm.

EXAMPLE C

| Tablets | Per Tablet |
| --- | --- |
| rac-1-[(9aβH)-7β-(o-fluorophenyl)octahydro-2H-quinolizin-2α-yl]-5-chloro-2-benzimidazoline HCl | 10.0 mg. |
| Lactose | 129.0 mg. |
| Maize starch | 50.0 mg. |
| Gelatinized maize starch | 8.0 mg. |
| Calcium stearate | 3.0 mg. |
| Total Weight | 200.0 mg. |

The rac-1-[(9aβH)-7β-(o-fluorophenyl)octahydro-2H-quinolizin-2α-yl]-5-chloro-2-benzimidazoline hydrochloride, the lactose, the maize starch and the gelatinized maize starch are intimately mixed with one another. The mixtue is passed through a comminuting machine and subsequently moistened with water to a thick paste. The moist mass is passed through a sieve. The moist granulate is dried at 45° C. The dried granulate is mixed thoroughly with the calcium stearate. The granulate is now pressed to tablets weighing 200 mg. and having a diameter of about 8 mm.

EXAMPLE D

| Tablets | Per Tablet |
| --- | --- |
| (−)-(2S,7R,9aR)-2-Tert.butyl-7-(2,4-dichlorophenyl)octahydro-2H-quinolizin-2-ol HCl | 20.0 mg. |
| Lactose | 115.0 mg. |
| Maize starch | 61.0 mg. |
| Talc | 3.4 mg. |
| Magnesium stearate | 0.6 mg. |
| Total Weight | 200.0 mg. |

The ingredients are intimately mixed with one another and pressed to tablets each weighing 200 mg. Subsequently, the tablets are coated with ethyl cellulose and Carbowax.

EXAMPLE E

| Capsules | Per Capsule |
| --- | --- |
| rac-1-[(9aβH)-7β-(o-fluorophenyl)octahydro-2H-quinolizin-2α-yl]-5-chloro-2-benzimidazolone HCl | 10.0 mg. |
| Lactose | 175.0 mg. |
| Maize starch | 30.0 mg. |
| Talc | 5.0 mg. |
| Total Weight | 220.0 mg. |

The rac-1-[(9aβH)-7β-(o-fluorophenyl)octahydro-2H-quinolizin-2α-yl]-5-chloro-2-benzimidazolone hydrochloride, the lactose and the maize starch are intimately mixed with one another and passed through a comminuting machine. The mixtue is now mixed thoroughly with the talc and filled into hard gelatin capsules.

EXAMPLE F

| Capsules | Per Capsule |
| --- | --- |
| (+)-2-Butyloctahydro-7-phenyl-2H-quinolizin-2-yl acetate HCl | 10.0 mg. |
| Lactose | 175.0 mg. |
| Maize starch | 30.0 mg. |
| Talc | 5.0 mg. |
| Total Weight | 220.0 mg. |

The (+)-2-butyloctahydro-7-phenyl-2H-quinolizin-2-yl acetate hydrochloride, the lactose and the maize starch are intimately mixed with one another and passed through a comminuting machine. The mixture is now mixed thoroughly with the talc and filled into hard gelatin capsules.

EXAMPLE G

| Parenteral administration form (0.2 mg) | |
| --- | --- |
| Each 1 ml. ampul contains: | |
| rac-1-[(9aβH)-7β-(o-fluorophenyl)octahydro-2H-quinolizin-2α-yl]-5-chloro-2-benzimidazolone HCl | 0.204 mg. (2% excess) |
| Glucose for injection | 40.0 mg. |
| Water for injection q.s. ad | 1.0 ml. |

2.04 g. of rac-1-[(9aβH)-7β-(o-fluorophenyl)octahydro-2H-quinolizin-2α-yl]-5-chloro-2-benzimidazolone hydrochloride are treated with 400 g. of glucose, dissolved in water for injection, and made up to a volume of 10,000 ml. with water for injection. The solution is either filtered sterile and filled into colorless ampuls which are gassed with nitrogen and sealed or filled into colorless ampuls which are gassed with nitrogen, sealed and subsequently sterilized with a current of steam for 30 minutes or autoclaved at 120° C.

EXAMPLE H

| Parenteral administration form (0.5 mg) | |
| --- | --- |
| Each 1 ml. ampul contains: | |
| (+)-2-Butyloctahydro-7-phenyl-2H-quinolizin-2-yl acetate HCl | 0.510 mg. (2% excess) |
| Glucose for injection | 40.0 mg. |
| Water for injection q.s. ad | 1.0 ml. |

5.10 g. of (+)-2-butyloctahydro-7-phenyl-2H-quinolizin-2-yl acetate hydrochloride are treated with 400 g. of glucose, dissolved in water for injection, and made up to a volume of 10,000 ml. with water for injection. The solution is either filtered sterile and filled into colorless ampuls which are gassed with nitrogen and sealed or filled into colorless ampuls which are gassed with nitrogen, sealed and subsequently sterilized with a current of steam for 30 minutes or autoclaved at 120° C.

We claim:

1. A compound of the formula

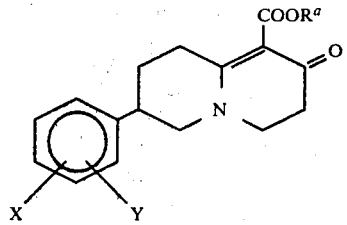

XIII wherein X is hydrogen, fluorine, chlorine, lower alkoxy, lower alkyl or trifluoromethyl; Y is hydrogen, fluorine, chlorine, lower alkoxy or lower alkyl; and $R^a$ is lower alkyl.

2. A compound of the formula

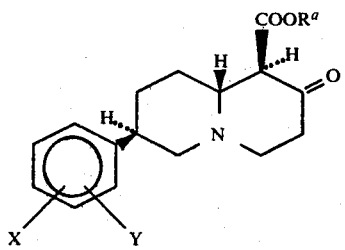

XIV wherein X is hydrogen, fluorine, chlorine, lower alkoxy, lower alkyl or trifluoromethyl; Y is hydrogen, fluorine, chlorine, lower alkoxy or lower alkyl; and $R^a$ is lower alkyl, its racemate or an enantiomer thereof.

3. A compound of the formula

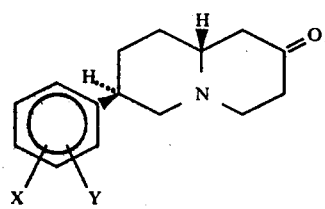

V wherein X is hydrogen, fluorine, chlorine, lower alkoxy, lower alkyl or trifluoromethyl; and Y is hydrogen, fluorine, chlorine, lower alkoxy or lower alkyl, its racemate or an enantiomer thereof.

4. Rac-(9aβH)-7β(o-chlorophenyl)octahydro-2H-quinolizin-2-one.

* * * * *